US010383417B2

(12) United States Patent
Fawcett et al.

(10) Patent No.: US 10,383,417 B2
(45) Date of Patent: Aug. 20, 2019

(54) CONTACT LENS CASE AND RELATED METHODS AND KITS

(71) Applicant: CooperVision International Holding Company, LP, St. Michael (BB)

(72) Inventors: Lisa Fawcett, Pittsford, NY (US); Aldo Zucaro, Webster, NY (US); James Lonnen, Henley-on-Thames (GB); Glenn Harrison, Andover (GB); Melanie George, Berkeley, CA (US); Andrew Luk, Pleasanton, CA (US); Kevin Barrett, Tyne and Wear (GB); Gary Hunt, Bristol (GB); Matthew Sultan Yan, Bristol (GB); Roya Borazjani, Newport Coast, CA (US)

(73) Assignee: CooperVision International Holding Company, LP, St. Michael (BB)

( * ) Notice: Subject to any disclaimer, the term of this patent is extended or adjusted under 35 U.S.C. 154(b) by 0 days.

(21) Appl. No.: 15/802,480

(22) Filed: Nov. 3, 2017

(65) Prior Publication Data
US 2018/0116357 A1    May 3, 2018

Related U.S. Application Data

(62) Division of application No. 15/335,836, filed on Oct. 27, 2016, now Pat. No. 9,839,271.

(51) Int. Cl.
*A45C 11/00* (2006.01)
*B65B 7/16* (2006.01)
(Continued)

(52) U.S. Cl.
CPC .......... *A45C 11/005* (2013.01); *A45C 11/008* (2013.01); *A61L 2/23* (2013.01);
(Continued)

(58) Field of Classification Search
CPC ....... A45C 11/005; A45C 11/008; A61L 2/23; A61L 12/08; A61L 2202/17;
(Continued)

(56) References Cited

U.S. PATENT DOCUMENTS 3,089,500 A    5/1963 Stalcup
3,460,552 A    8/1969 Sturgeon
(Continued)

FOREIGN PATENT DOCUMENTS

DE      9216029 U1      1/1993
JP      H07237682 A     9/1995
WO      2013182849 A1  12/2013

OTHER PUBLICATIONS

Extended European Search Report issued in corresponding European Patent Application No. 16196125.5 dated May 22, 2017 (9 pages).
(Continued)

*Primary Examiner* — Jacob K Ackun
*Assistant Examiner* — Jenine Pagan
(74) *Attorney, Agent, or Firm* — Kilyk & Bowersox, P.L.L.C.

(57) ABSTRACT

A case is provided for holding one or more contact lenses. The case is configured to receive an inner pod, and the case includes an upper part and a lower part. The upper part is structured to move relative to the lower part from an open configuration wherein the upper and lower parts are at least partially separated to a closed configuration wherein the upper and lower parts are together. The upper part is also structured to move relative to the lower part from a disengaged position to an engaged position wherein, in the disengaged position, the case is movable between the open and closed configurations and in the engaged position, the case is locked in the closed configuration.

3 Claims, 16 Drawing Sheets

(51) Int. Cl.
*B65D 81/22* (2006.01)
*B65B 5/04* (2006.01)
*A61L 12/08* (2006.01)
*A61L 2/23* (2006.01)

(52) U.S. Cl.
CPC ............... *A61L 12/08* (2013.01); *B65B 5/04* (2013.01); *B65B 7/16* (2013.01); *B65D 81/22* (2013.01); *A61L 2202/17* (2013.01); *A61L 2202/23* (2013.01); *B65D 2585/545* (2013.01)

(58) Field of Classification Search
CPC ......... A61L 2202/23; B65B 5/04; B65B 7/16; B65D 81/22; B65D 2585/545
USPC ..... 206/5.1, 205, 207, 210; 422/292, 40, 28, 422/300; 134/901
See application file for complete search history.

(56) References Cited

U.S. PATENT DOCUMENTS

| | | | |
|---|---|---|---|
| 3,856,571 A | 12/1974 | Sherman | |
| 4,091,917 A | 5/1978 | Clawson et al. | |
| 4,406,362 A | 9/1983 | Thomas et al. | |
| 4,823,944 A | 4/1989 | Ryder | |
| 5,129,999 A | 7/1992 | Holland et al. | |
| 5,297,687 A | 3/1994 | Freed | |
| 5,365,630 A | 11/1994 | Beckrich | |
| 5,439,572 A | 8/1995 | Pankow | |
| 5,871,702 A | 2/1999 | Kutner et al. | |
| 6,244,430 B1 | 6/2001 | Travis | |
| 6,343,399 B1* | 2/2002 | Pankow | A45C 11/005 15/104.92 |
| 6,868,963 B2 | 3/2005 | Borovsky | |
| 7,000,960 B2* | 2/2006 | Py | A45C 11/005 206/5.1 |
| 8,015,987 B2 | 9/2011 | Zakutin | |
| 8,069,979 B2 | 12/2011 | Newman et al. | |
| 2005/0133382 A1 | 6/2005 | Gerard et al. | |
| 2008/0264804 A1* | 10/2008 | Newman | A45C 11/005 206/5.1 |
| 2009/0211925 A1* | 8/2009 | Doniga | A45C 11/005 206/5.1 |

OTHER PUBLICATIONS

U.S. Appl. No. 15/335,836, filed Oct. 27, 2016 (53 pages).
Design U.S. Appl. No. 29/582,504, filed Oct. 28, 2016 (7 pages).
Design U.S. Appl. No. 29/582,505, filed Oct. 28, 2016 (7 pages).
Design U.S. Appl. No. 29/582,507, filed Oct. 28, 2016 (15 pages).
Combined Search and Examination Report issued in United Kingdom Patent Application No. GB1618205.7 dated Mar. 17, 2017 (7 pages).

* cited by examiner

CONTACT LENS CASE AND RELATED METHODS AND KITS

This application is a divisional application of U.S. patent application Ser. No. 15/335,836, filed Oct. 27, 2016.

FIELD OF THE INVENTION

The present invention relates to the field of contact lens cases. In particular, but not exclusively, the invention provides re-sealable cases for contact lenses.

BACKGROUND OF THE INVENTION

Contact lenses, other than daily disposable contact lenses, are usually stored in a lens care solution over-night to clean the contact lenses prior to wear the next day. During this process, worn contact lenses are placed in a contact lens case that contains a lens care solution. An example of a contact lens case for cleaning contact lenses is made from a rigid plastics material and has two side-by-side dishes (one for each lens) into which lens care solution is dispensed, and two screw-top lids (one for each dish). Since these cases are re-used many times, and are not typically stored in sterile conditions, they are not sterile and thus are prone to microbial accumulation. A further problem is that the user may on different occasions wish to use different lens care solutions; using these lens care cases can lead to cross-contamination between solutions.

Another example of a contact lens care case is a tall clear plastic case filled with lens care solution, having a single well or dish (defined by the case), and having a screw-cap lid to which an arm is attached. The arm is submerged in the solution in the single well when the lid is screwed onto the case. At the end of the arm are two hinged cages, one for each lens, for holding the lenses in the solution. The lenses are completely submerged in the solution but nonetheless, may be contaminated initially and during re-use of the case.

The present invention seeks to mitigate the above-mentioned problems. Alternatively or additionally, the present invention seeks to provide an improved contact lens case.

SUMMARY OF THE INVENTION

Briefly and in general terms, the present invention provides apparatus and methods directed towards improved contact lens cases.

The invention provides in a first aspect, a case for holding one or more contact lenses, the case having the features set out below.

The invention provides in a second aspect a method of treating a contact lens including the steps set out below.

The invention provides in a third aspect a method of treating a contact lens including the steps set out below.

The invention provides in a fourth aspect a kit of parts for holding one or more contact lenses, the kit having the features set out below.

It will be appreciated that features described in relation to one aspect of the present invention may be incorporated into other aspects of the present invention. For example, the method of the invention may incorporate any of the features described with reference to the apparatus of the invention and vice versa. Moreover, additional embodiments and aspects will be apparent from the following description, drawings, and claims. As can be appreciated from the foregoing and following description, each and every feature described herein, and each and every combination of two or more of such features, and each and every combination of one or more values defining a range, are included within the scope of the present disclosure provided that the features included in such a combination are not mutually inconsistent. In addition, any feature or combination of features or any value(s) defining a range may be specifically excluded from any embodiment of the present disclosure.

DESCRIPTION OF THE DRAWINGS

An embodiment of the present invention will now be described by way of example only with reference to the accompanying drawings of which.

DETAILED DESCRIPTION

Figure 1:
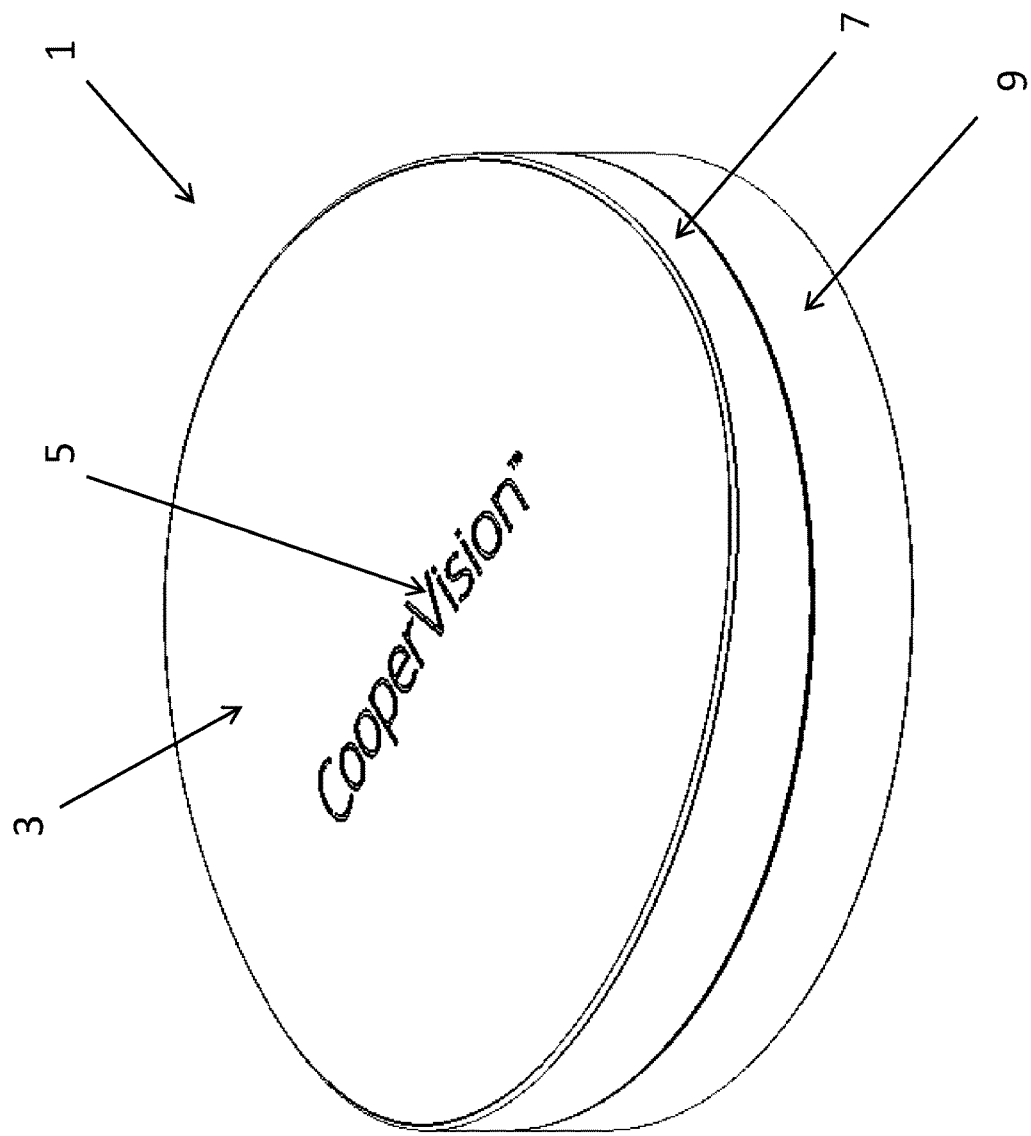
FIG. 1 is a perspective view of the exterior of a contact lens case in the example embodiment of the invention in a closed and engaged arrangement.

Embodiments are described herein in the context of improved cases for contact lenses.

Those of ordinary skill in the art will realise that the following detailed description is illustrative only and is not intended to be in any way limiting. Other embodiments of the present invention will readily suggest themselves to such skilled persons having the benefit of this disclosure. Reference will be made in detail to implementations as illustrated in the accompanying drawings. The same reference indicators will be used throughout the drawings and the following detailed description to refer to the same or like parts.

As previously stated, a first aspect is directed to a case for holding one or more contact lenses. The case is configured to receive a (removable) inner pod. The case comprises an upper part and a lower part. The upper part is structured to move relative to the lower part from an open configuration wherein the upper and lower parts are at least partially separated to a closed configuration wherein the upper and lower parts are together, and the upper part is structured to move relative to the lower part from a disengaged position to an engaged position wherein, in the disengaged position, the case is movable between the open and closed configurations and in the engaged position, the case is locked in the closed configuration.

The case provides a shell into which pods containing a variety of solutions may be placed, thus allowing the user to easily switch between different lens care solutions, without cross-contamination. The present invention is preferably portable and visually appealing.

In the disengaged position, the upper and lower parts of the case may be misaligned. Preferably, the case is substantially elliptic cylindrical in shape, so that as the upper part is rotated with respect to the lower part, the case moves from an aligned position wherein the upper and lower parts completely overlap (the engaged position), to a misaligned position wherein the upper and lower parts partially overlap (the disengaged position). The misalignment may be between 30 to 40 degrees. The misalignment may be between 20 to 50 degrees. Existing lens care cases typically have circular screw-top lids. When using those cases, the user may not easily be able to determine whether the screw-top lid has been correctly fitted, and solution can leak from the case during transportation. In the present cases disclosed herein, the misalignment may be visible (or otherwise detectable) to the user. Any misalignment (i.e. with respect to the engaged position) may alert the user to the disengaged state of the case.

The case may further include an inner pod, the inner pod comprising a base portion defining one or more compartments and a re-sealable lid, wherein, when the case is in the engaged position, the inner pod is compressed between the upper and lower parts, the upper part structured to apply pressure to the lid to seal the one or more compartments.

If a seal formed by replacement of a film lid on a pod is not water-tight, the pod may not be easily transportable, once opened, due to potential spillage and contamination. Advantageously, the seal formed in example embodiments of the invention is water-tight, preventing leakage of the solution during transportation and storage.

The present invention advantageously provides a sealable case for storing and/or transporting contact lenses in a lens care solution, the case also being re-useable. In contrast, existing sterile contact lens cases are typically single-use, disposable packs, for example blister packs, pre-filled with packaging solution for storing un-used, un-worn contact lenses. These single-use disposable packs are produced as part of the contact lens manufacturing process to provide sterile contact lenses to a user. On the other hand, existing re-useable lens care cases such as the screw-cap cases described above, are used for treating used lenses and are neither sterile nor intended for use with different lens care solutions. The present invention recognises that re-sealing an opened pod by applying pressure to its lid enables a user to treat (and transport) a used contact lens in a more hygienic environment. The present invention may therefore be particularly beneficial for frequent replacement contact lenses, other than daily disposable contact lenses.

The case may include a drain for draining liquid that would otherwise be retained in the case. It is important that the case itself cannot be used to store a lens directly, i.e. without an inner pod, because the case will generally not be sterile. Providing a drain ensures that the case cannot be filled with a liquid in which a user could attempt to store a contact lens. The drain may for example be in the form of a hole. The lower part may have one or more hole for receiving an inner pod; the hole(s) may then also function as the drain.

The inner pod may preferably have two compartments, one for each lens of a pair of contact lenses, but may alternatively have only one compartment, or more than two compartments.

Preferably, in the closed configuration, the inner pod is retained in the case and, in the open configuration, the inner pod is removable from the case. In the open configuration the upper and lower parts may be at least partially separated, the separation being wide enough that a pod can be placed in the case. In the closed configuration the upper and lower parts may be together, so that a pod may not be placed in (or removed from) the case.

The lid may be a film lid having a re-sealable first region and a second region that is fixed to the base portion. The film lid may be flexible and more easily compressible than a rigid lid. The film lid may be peelable and may include a layer of polypropylene. Preferably, the first and second regions of the lid are made of the same material. The second region (and/or a boundary between the first region and the second region) may be substantially parallel to a longer edge of the inner pod. The second region may be a strip running substantially parallel to a longer edge of the inner pod. The first region may be the entirety of the surface of the lid but excluding the second region. The second region may be fixed to the base portion by a permanent compression seal. The first region may be re-sealable by formation of a temporary compression seal.

Advantageously, the permanent seal in the second region prevents the lid being entirely removed by the user, for example, when the lid is peeled back so that lenses can be placed in the pod, hence preventing the lid being damaged or removed and lost. The permanent seal in the second region usefully may also or alternatively ensure correct alignment of the lid with respect to the base portion when the lid is replaced, so that an effective liquid-tight seal is formed.

It may be that the inner pod is in an un-used condition having an unbroken initial compression seal between the lid and the base portion. The unbroken initial seal may be over substantially the entire top surface of the base portion, encompassing the first and second regions. The unbroken initial seal may be water-tight.

Alternatively, it may be that the inner pod is in a used condition, having a broken initial seal between the lid and the base portion. In the used configuration, the lid may be replaced on the base portion. The replacement of the lid may be a useful intermediate step, preventing spilling of solution when the inner pod is placed inside the case. The lid may also be re-sealed, preferably giving a water-tight seal, to the base portion around the compartments.

It may be that the lid seals the one or more compartments in a region around the compartments, the seal being closer to the compartments than to the outer edge of the lid. The seal may be formed by compression of the inner pod. The location of the seal may minimise loss of solution from the compartments, thus ensuring the lenses remain fully submerged in the solution. In an alternative embodiment of the invention it may be that the re-seal is formed directly between the upper part and the inner pod, for example, without the lid.

The upper part may comprise a cover mounted on a compression member, the cover mounted for movement such that the cover rotates with respect to the compression member.

The upper part may include an annulus, the annulus positioned between the cover and the compression member, arranged to apply pressure to the compression member when the case is in the engaged position. The annulus may be fixed to the compression member and loosely connected to the cover. The annulus may interact with the cover so as to limit its rotational movement (relative to the compression member). The term annulus will be understood to mean a substantially ring-shaped member. Such a member may be a loop or a hoop, incorporating recesses and/or protrusions.

The cover may have recesses to accommodate protrusions on the outer surface of the annulus, so that when the case transitions between the engaged and disengaged positions, the protrusions move between the recesses as the cover rotates with respect to the annulus. The annulus may have resting positions defined by the location of the recesses. It may be that the annulus is biased to remain in the one or more resting positions. It may be that a threshold force must be applied to urge the annulus out of the one or more resting positions. Advantageously, the location of the resting positions determines the maximum misalignment of the cover with respect to the compression member.

It may be that, when the case transitions between open and closed configurations, the annulus remains fixedly connected to both the compression member and cover.

The cover may have grooves to accommodate protrusions on the outer surface of the annulus, so that when the case transitions between engaged and disengaged positions, the annulus remains fixedly connected to the compression member, whilst the cover moves with respect to both the compression member and annulus.

The compression member may comprise an elastomeric material. The elasticity of the elastomeric compression member may enable a water-tight seal to be formed around the one or more compartments of the inner pod. The elastomeric compression member may be in the form of a sheet, for example a rubber sheet.

The compression member may have one or more raised portions and, in the engaged position, the one or more raised portions of the compression member may contact the lid, forming a seal underneath the one or more raised portions.

The seal may preferably have a different locus to (that is, be in a different place from) the initial seal between the lid and the base portion. The seal may be more targeted, for example. The seal may have a smaller surface area than the initial seal. The raised portions may form a ridge, preferably a continuous ridge around the compartments. Pressure applied via a small surface area, for example, a ridge, may provide a stronger seal than if the same pressure were applied over a larger surface area. The raised portions may resemble a figure-eight enclosing the compartments.

The lower part may have a threaded portion and the upper part may have a threaded portion and rotation from the disengaged to the engaged position may cause the threaded portions to interlock such that the inner pod is compressed. The threaded portions may be located towards the outer perimeter of the apparatus. The threaded portions may be a continuous helix. More preferably, the threaded portions may be a broken helix (e.g. small sections of a helix). It may be that a rotational adjustment of less than 50 degrees is required to move from the engaged position to the disengaged position; it may be that a rotational adjustment of less than 40 degrees is required. This can be contrasted with existing lens care cases described above having a screw-cap lid, in which rotation of at least 360 degrees is typically required to remove the lid. The example embodiment of the present invention may thus be quicker and simpler to use than existing lens care cases.

In the open position, the inner pod may be releasably retained in the case. It is advantageous for the case to grip or otherwise hold in place the inner pod once the pod is placed in the case, for example so that the resealable lid of the pod can be removed while the pod is in the case. Advantageously, the opened pod can be held in place until the user removes it to replace it with a new inner pod.

The case may include one or more retaining clips for holding the inner pod within the case. There may be two retaining clips, for retaining opposing ends of the inner pod. The retaining clips may bias the inner pod to remain within the case.

The upper part may be connected to the lower part by a hinge comprising an axle in a recess. The lower part may have a recessed portion and the upper part may have a corresponding protruding portion to form the hinge. The protruding and recessed portions may each have a tubular recess to accommodate the axle.

Preferably, the compression member is directly connected to the lower part by the hinge, whilst the cover is directly connected to the lower part by the threaded portions. The cover may only be indirectly connected to the lower part by the hinge via the compression member and annulus. Thus, the protruding portion may be on the compression member of the upper part.

The hinge may be configured to accommodate vertical movement of the axle within the recess.

The tubular recess in the lower part may have a circular cross-section. The tubular recess in the compression member may have an elongated circular cross-section, having a height greater than its width to enable the axle to move vertically within the recess when the cover is screwed on (and the plunger moves down). The tubular recess may thus enable compression of the inner pod when the cover is screwed onto the lower part.

The one or more compartments of the inner pod may contain a solution, for example a lens care solution, suitable for contact lenses.

The one or more compartments of the inner pod may contain one or more contact lenses immersed in solution. The solution may be a lens care solution. The lens care solution may contain preservatives, cleaning agents, wetting agents, and the like. The one or more contact lenses may be hydrogel contact lenses or silicone hydrogel contact lenses. The inner pod may be selected from a plurality of pods containing different solutions.

As previously stated, the second aspect provides a method of treating a contact lens including the following steps: providing a case for holding one or more contact lenses, the case comprising an upper part and a lower part; providing an inner pod comprising a base portion defining one or more compartments and a re-sealable lid; partially removing the lid of the inner pod; placing a contact lens in a compartment of the inner pod; replacing the lid of the inner pod; placing the inner pod on the lower part of the case; closing the case so that the inner pod is enclosed in the case; moving the upper part relative to the lower part so that the inner pod is compressed between the upper and lower parts and the lid seals the one or more compartments.

The method may include the step of removing a used inner pod from the case and discarding the used inner pod. The method may include the step of selecting the inner pod from a plurality of pods. The lid may seal the one or more compartments to form a water-tight seal between the lid and the base portion.

In addition, the method of the second aspect may use an inner pod having one or more compartments that contain a solution, for example a lens care solution, suitable for contact lenses.

As previously stated, the third aspect provides a method of treating a contact lens including the steps of: providing a case for holding one or more contact lenses, the case comprising an upper part and a lower part, wherein the case is in an open arrangement in which the upper and lower parts are pivotally separated; providing an inner pod comprising a base portion defining one or more compartments and a re-sealable lid; partially removing the lid of the inner pod; placing a contact lens in a compartment of the inner pod; replacing the lid of the inner pod; placing the inner pod on the lower part of the case; moving the case from the open arrangement to a closed and disengaged arrangement in which the upper and lower parts are not pivotally separated and the upper and lower parts are misaligned and the inner pod is not compressed between the upper and lower parts; moving the case from the closed and disengaged arrangement to a closed and engaged arrangement in which the upper and lower parts are not pivotally separated and the upper and lower parts are aligned and the inner pod is compressed between the upper and lower parts and the lid seals the one or more compartments.

In addition, the method of the third aspect may use an inner pod having one or more compartments that contain a solution, for example a lens care solution, suitable for contact lenses.

As previously stated, the fourth aspect provides a kit of parts for holding one or more contact lenses including: a plurality of inner pods, each inner pod including a base portion defining one or more compartments and a re-sealable lid; a case for receiving an inner pod selected from the plurality of inner pods, the case comprising an upper part and a lower part, the upper part structured to move relative to the lower part from an open configuration wherein the upper and lower parts are at least partially separated so that the inner pod may be placed in the case, to a closed configuration wherein the upper and lower parts are together, and, the upper part structured to move relative to the lower part from an engaged position to a disengaged position wherein, in the engaged position the case is locked in the closed configuration, and in the disengaged position the case is movable between the open and closed configurations.

The inner pod may contain a solution of a first composition and the plurality of pods may include at least one second inner pod containing a solution of a second, different, composition.

As an example, the inner pod has one or more compartments that contain a solution, for example a lens care solution, suitable for contact lenses. And, if a plurality of pods are provided with different solutions, it may be understood that the solutions are different contact lens care solutions.

In the present kits disclosed herein, a bottle of solution may also be provided. It will be understood that this bottle of solution is in addition to the solution(s) that are provided in the one or more inner pods, or more specifically, in the compartment(s) of the one or more inner pod(s). The solution in the bottle may be a rinsing solution effective in rinsing the contact lenses, or the solution may be a disinfecting solution suitable for reducing microbial content of the contact lenses.

In some of the present kits, one or more disinfectant wipes may be provided. That is, a kit according to the present disclosure may include at least one disinfectant wipe. In some embodiments, a plurality of disinfectant wipes (i.e., more than one) are provided. The disinfectant wipe includes a disinfecting agent suitable for cleaning a substrate. The disinfectant wipe may be effective in cleaning a contact lens, or the disinfectant wipe may be effective in cleaning the cases disclosed herein, or one or more components thereof.

The kit may be provided as any suitable device, which can contain the contact lens case described herein, the plurality of inner pods, and optionally, a bottle of solution, as described above. For example, a box may be used to contain the plurality of inner pods and the contact lens case, and the optional bottle.

In view of the disclosure herein, an embodiment of the present invention can be understood to be a contact lens case configured to accommodate at least one removable inner pod, in which the inner pod has one or more compartments or wells containing a solution useful for soaking a contact lens.

If one inner pod is used with the case, the one inner pod may comprise two compartments, each compartment configured to contain a single contact lens. If two inner pods are used with the case, each inner pod may comprise a single compartment configured to contain a single contact lens. The at least one inner pod includes a contact lens care solution, as described herein, and is sealed with a flexible lid so that the contact lens care solution can be stored in the pod compartment under sterile conditions until the compartment is opened.

The lens care case has an open configuration in which the at least one inner pod can be inserted into the case or removed from the case. When the at least one inner pod is present in the case, the flexible lid can be removed so that a worn contact lens can be placed in the solution in the compartment of the inner pod. The flexible lid can then be placed over the compartment containing the solution and the worn contact lens.

The lens care case also has a closed configuration in which the flexible lid is pressed against a surface of the inner pod to provide a fluid tight seal to prevent leakage of the lens care solution from the compartment. Thus, in the closed configuration, the worn contact lens can be soaked in the lens care solution without having the lens care solution leaking and without additional unwanted contamination. Subsequently, the lens care case can be opened again to provide access to the compartment of the inner pod so that the treated worn contact lens can be reapplied to the contact lens wearer's eye.

An example embodiment of the invention will now be described with reference to the drawings.

The Components

Contact lens case 1 (see FIG. 1) has a broadly elliptic-cylindrical shape, with an approximately hyperbolic paraboloid upper surface 3 and a lower textured surface for gripping a surface such as a table top (not shown). The case 1 has a smooth outer surface and is approximately 9 cm by 8 cm by 2.5 cm in size. The case 1 is divided through a plane at its approximate mid-height forming an upper part 7 and a lower part 9. Text 5 is provided on the upper surface 3 which, as well as providing branding information in this example, aids the user in determining the correct orientation of the case 1 for use. The case 1 is manufactured by injection moulding using a conventional UV resistant and antibacterial plastics material.

In a first arrangement (as shown in FIG. 1), the case 1 is shut and fastened. The case 1 is in the closed configuration and the engaged position. The case 1 encloses an inner pod (not shown), the pod having compartments filled with solution in which contact lenses are placed (in another embodiment there may be no pod or more than one pod). There is a water-tight seal around the compartments of the pod. The contact lens case when in the first arrangement is suitable for transporting or storing contact lenses since the water-tight seal prevents leakage of the solution from the compartments of the inner pod.

After storage or transport, the user may wish to remove the contact lenses from the case 1. The case 1 is then moved through second and third arrangements so that the contact lenses may be retrieved.

Figure 2:
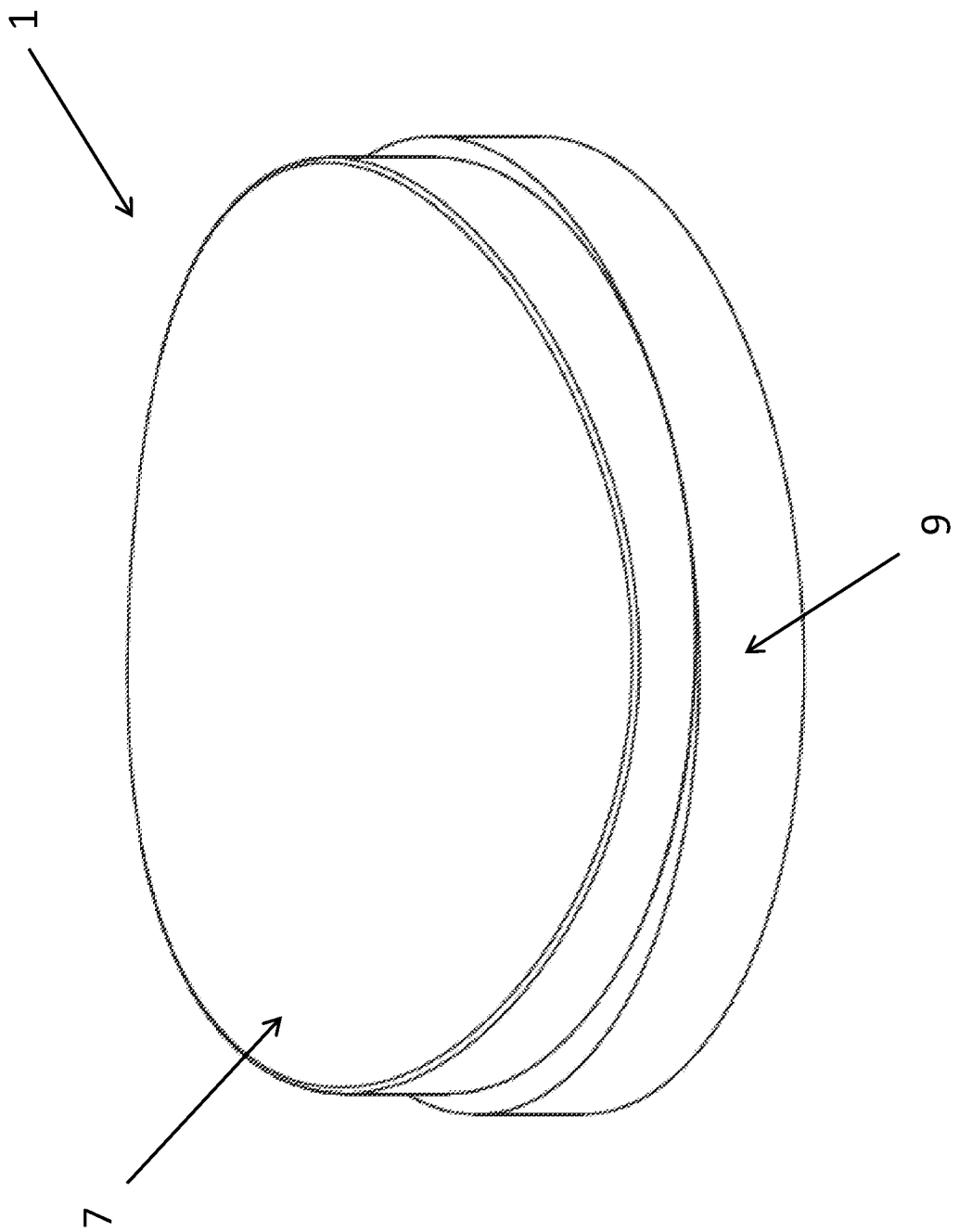
FIG. 2 is a perspective view of the exterior of the example case of FIG. 1 in a closed and disengaged arrangement.

In the second arrangement (see FIG. 2), the upper part 7 is loosened from the lower part 9 (having been unscrewed). The case 1 is in the closed configuration and the disengaged position. In the second arrangement, the water-tight seal around the compartments of the inner pod (not shown) is released. The second arrangement is an intermediate arrangement between the first arrangement and the third arrangement.

Figure 3:
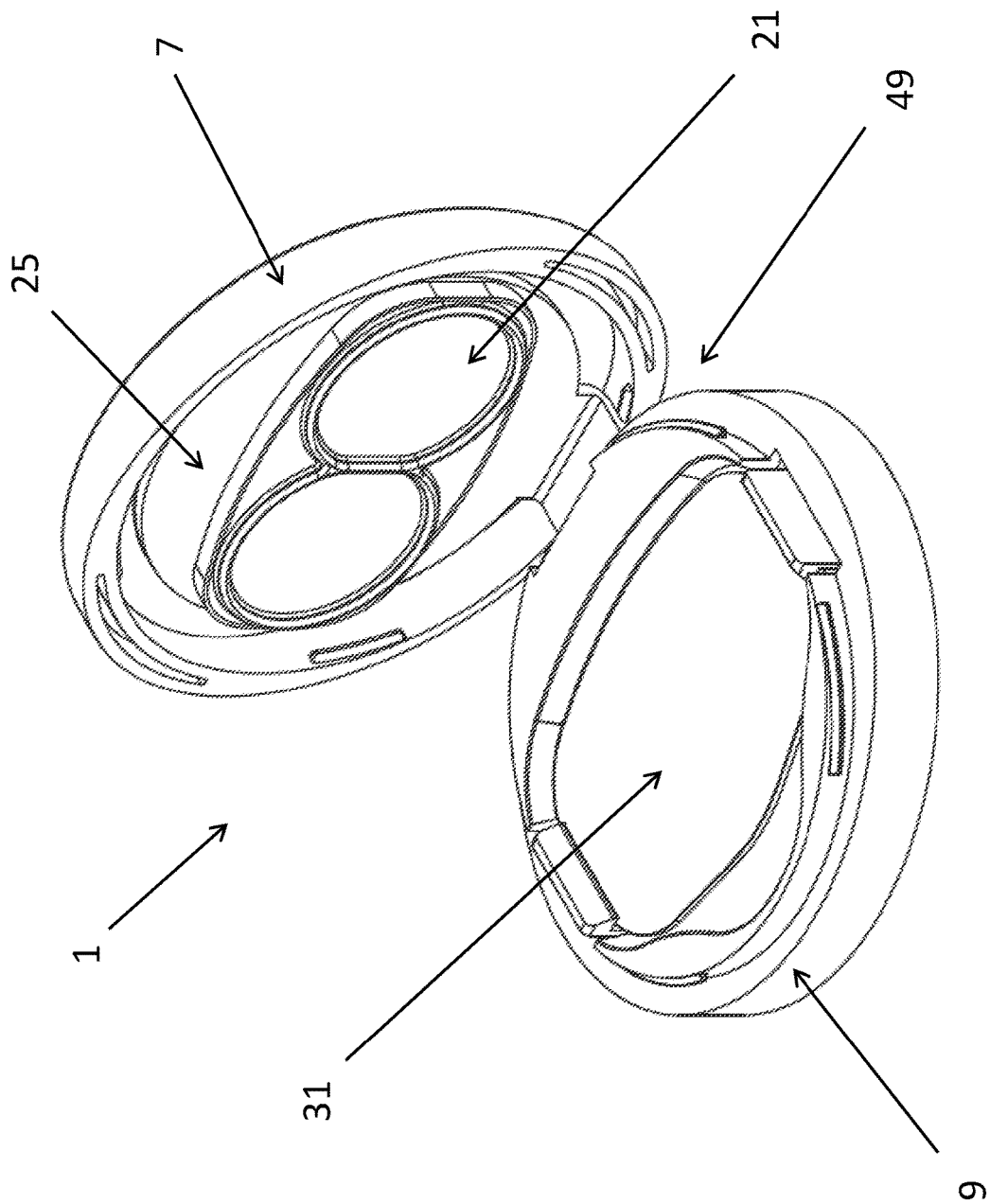
FIG. 3 is a perspective view of the exterior of the example case of FIG. 1 in an open arrangement.

In the third arrangement (see FIG. 3), the upper part 7 is opened about a hinge 49 (via the upper part 7 being lifted away from the lower part 9), revealing the pod 31 inside the case 1. The case 1 is in the open configuration and the disengaged position. The pod 31 rests in the lower part 9. Visible on the underside of the upper part 7 are a plunger 25 and a compression member 21. In the third arrangement, the user may remove the pod 31 from the case 1 and discard it. In FIG. 3, the pod 31 is illustrated with a film over two compartments of the pod. The user may then or later wish to place the contact lenses (or different contact lenses) in a new pod containing the same or a different solution and place that new pod in the case 1 for transport or storage.

The same steps may be enacted in reverse. When a pod 31 is placed inside the case 1, to secure a water-tight seal around the pod 31, the case 1 must be moved from the third to the second, and then to the first arrangement. The case 1 is shut (the upper part 7 being pushed down onto the lower part 9), moving the case 1 to the second arrangement (see FIG. 2). The case 1 is then screwed shut (i.e. moved into the first arrangement—FIG. 1) to form a water-tight seal around the compartments (not shown in FIGS. 1 to 3) of the pod 31.

Figure 4:
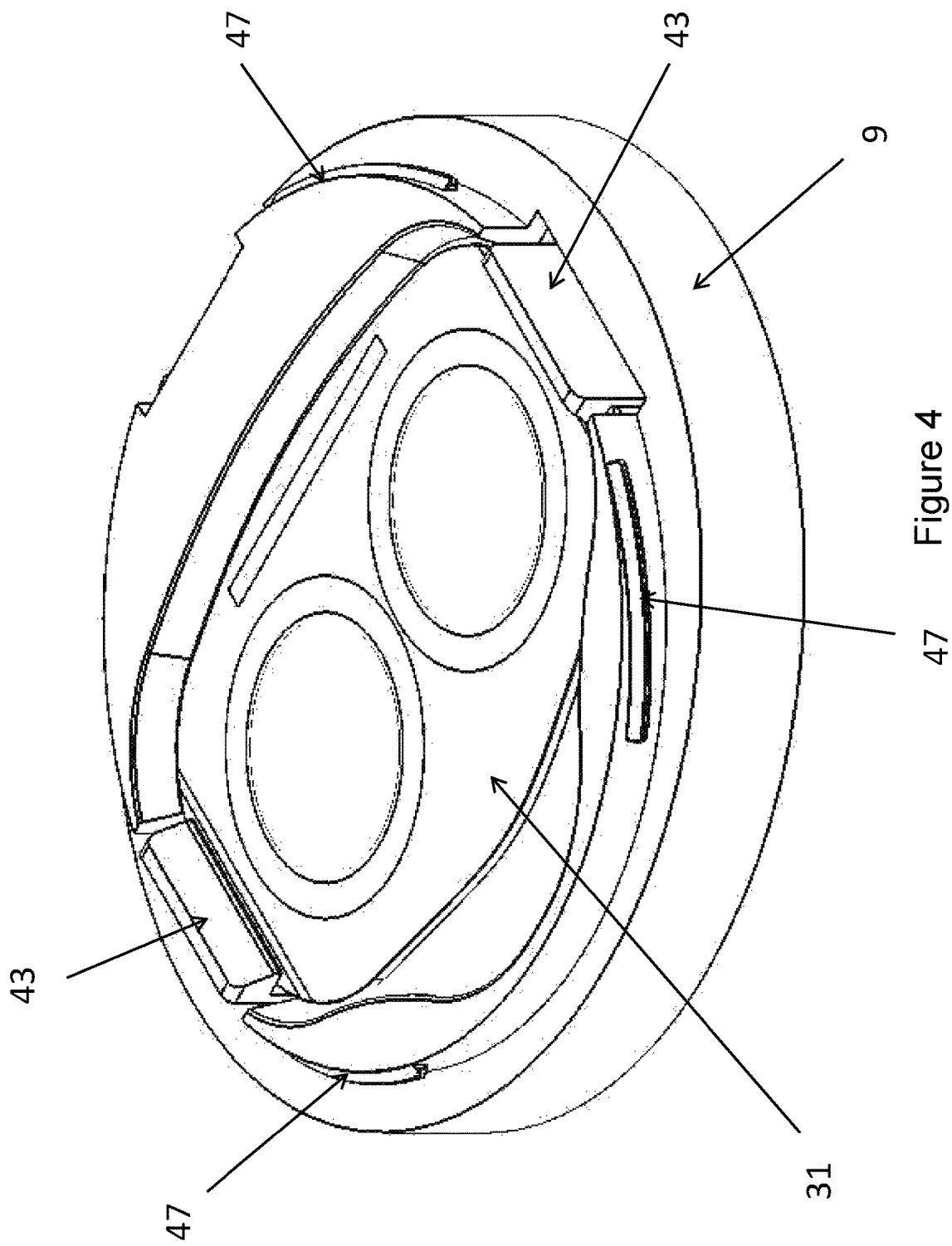
FIG. 4 is a perspective view of a lower part of the example case of FIG. 1 including the pod.
Figure 5:
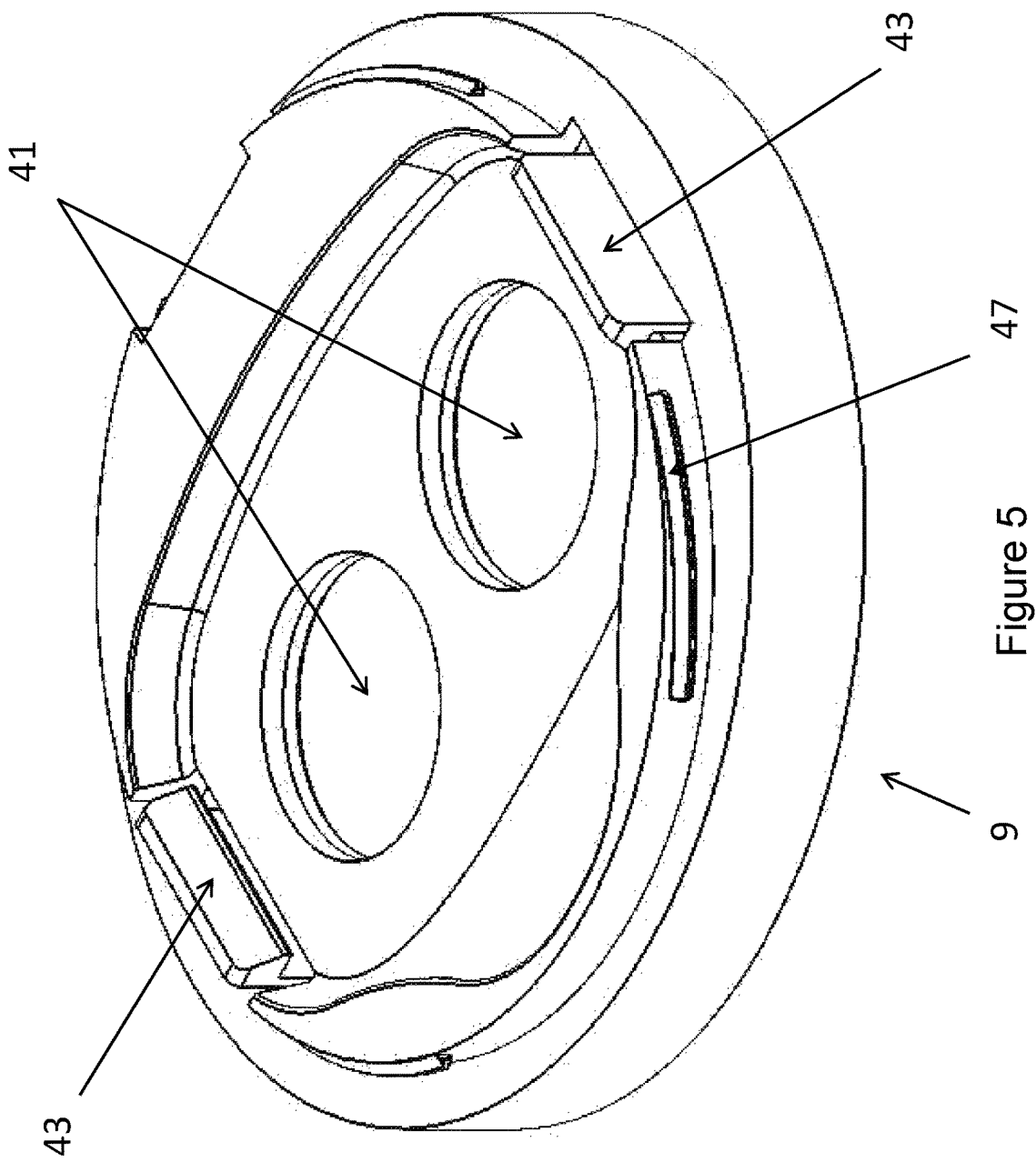
FIG. 5 is a perspective view of the lower part of the example case of FIG. 1 without the pod.

In the third arrangement, the user can see the inner pod 31 in the lower part 9 of the case 1. The lower part 9 (see FIGS. 4 and 5) of the case 1 is structured to hold pod 31. FIG. 4 shows the pod 31 in situ and FIG. 5 shows the lower part 9 with the pod 31 removed. The lower part 9 has two circular holes 41 for accommodating the pod 31. The circular holes 41 provide the additional advantage of preventing the case 1 from being directly filled with solution (i.e. from being used without a pod 31) because such liquid in the case would drain through the holes 41. At either side of the lower part 9 there are retaining clips 43, which lock the pod 31 in the lower part 9, preventing lateral movement during transportation. The lower part also has threaded portions 47 which form a partial helix inside the outer edge of the lower part 9. The threaded portions are positioned and sized to fit with corresponding threaded portions in the upper part 7.

Figure 6:
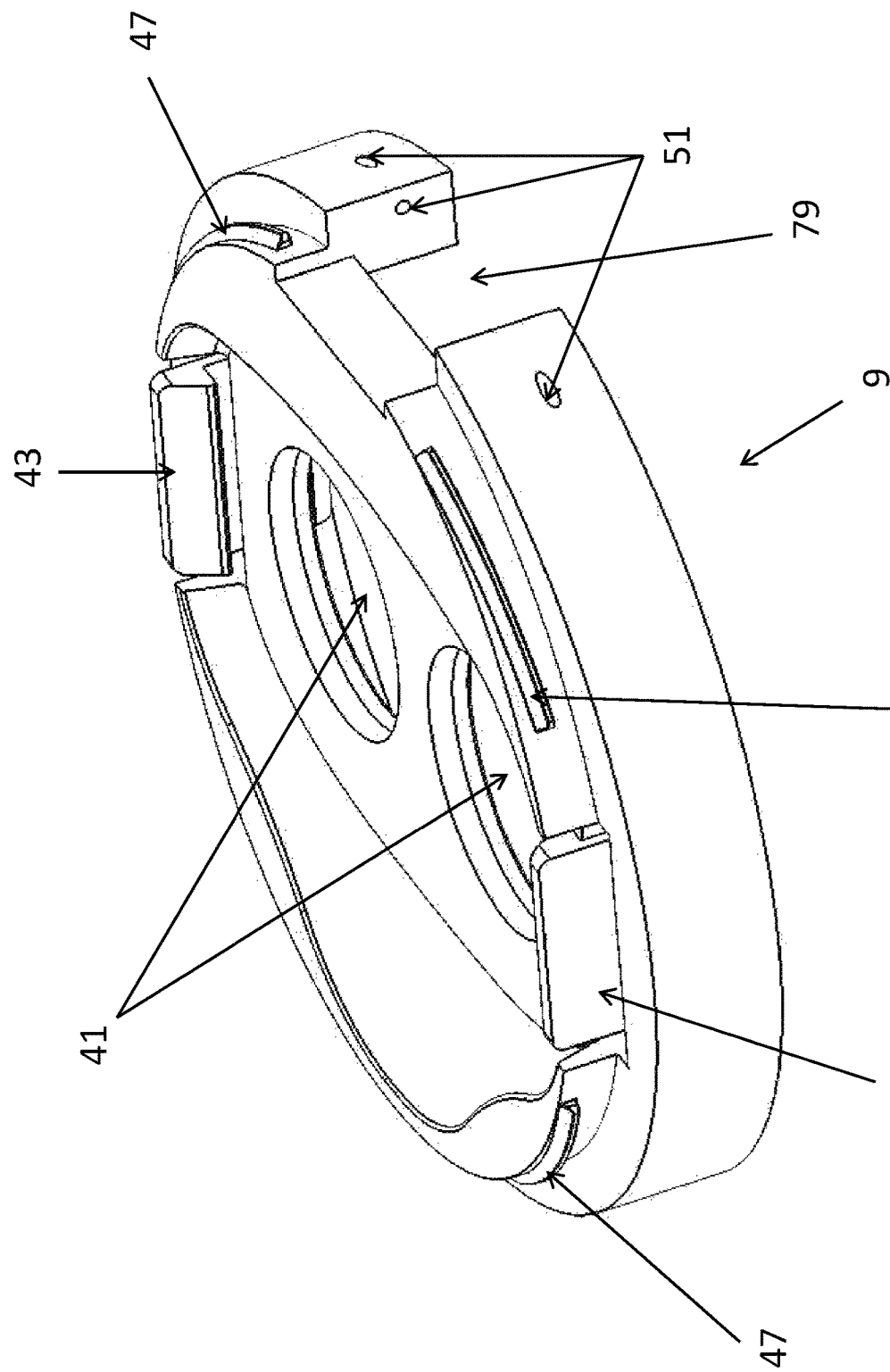
FIG. 6 is an alternative perspective view of the lower part of FIG. 1, showing in particular a hinge channel in the lower part.

At the back of the lower part 9 (see FIG. 6) a recessed portion 79 is visible. The recessed portion 79 forms part of a hinge with the upper part 7. The axle of the hinge (not shown) passes through a cylindrical void 51 in the lower part 9.

Figure 7:
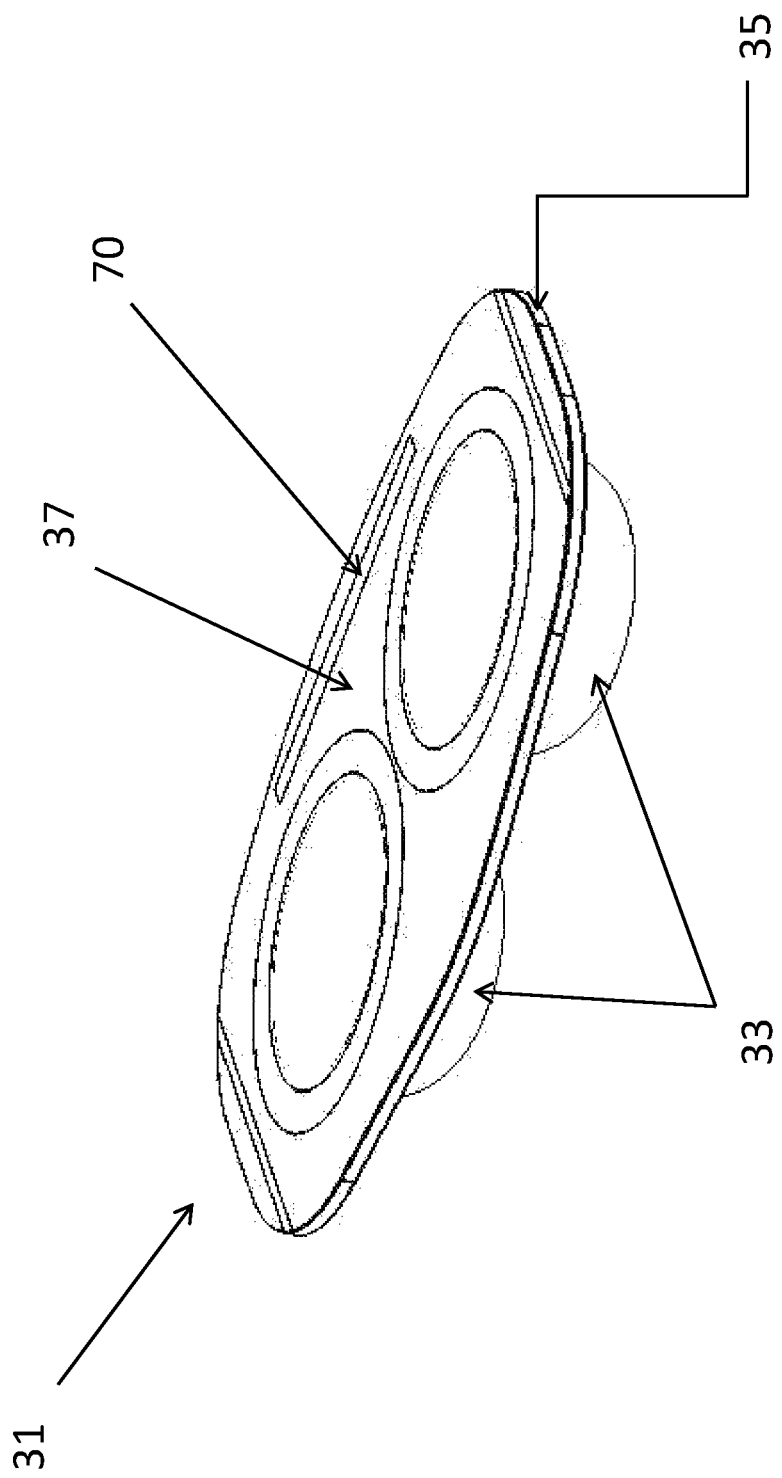
FIG. 7 is a perspective view of the pod.
Figure 8:
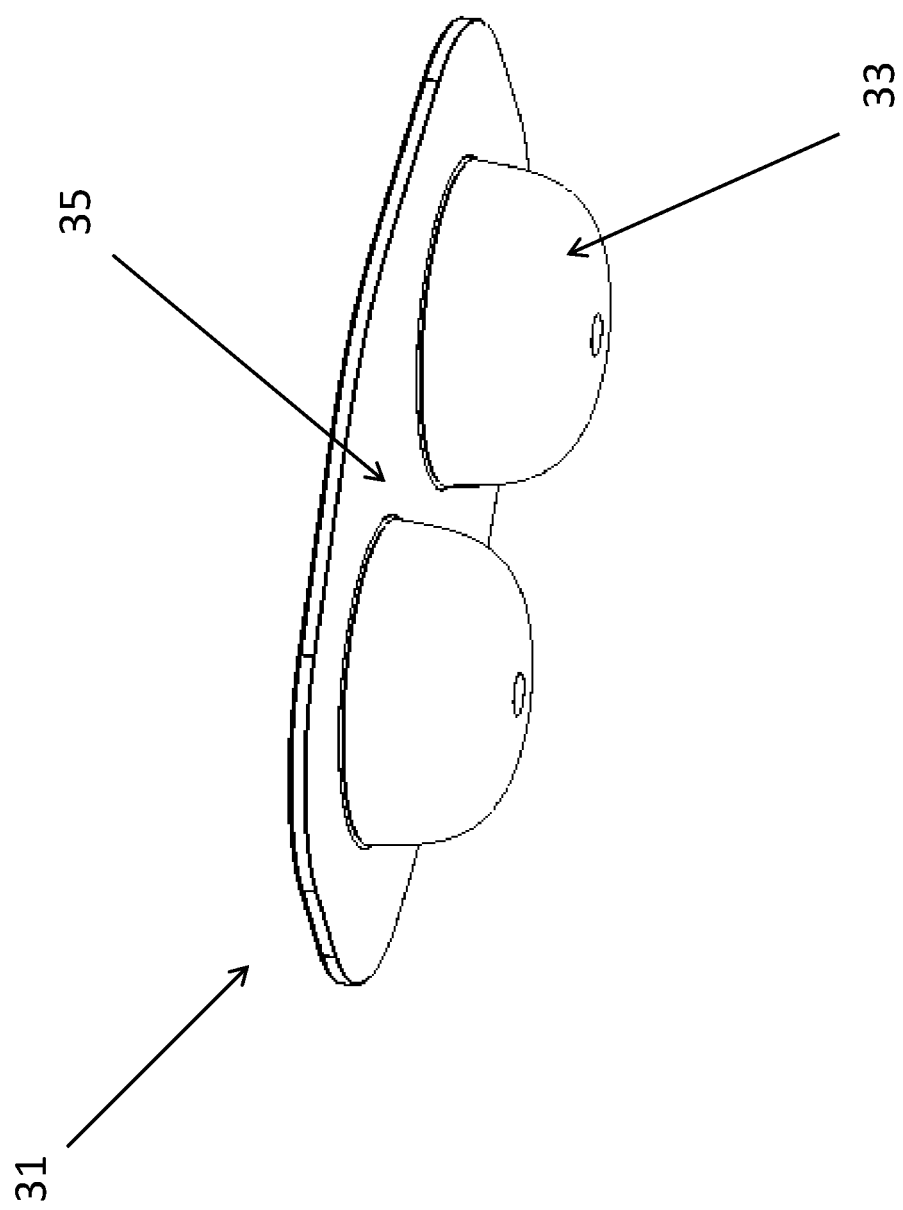
FIG. 8 is an alternative perspective view of the pod.

The inner pod 31 (see FIGS. 7 and 8) has a base portion 35 defining two substantially hemi-spherical compartments 33 and is formed of polyethylene terephthalate (however, other plastic materials may be used). The inner pod 31 also has a covering film lid 37 formed of metallic foil and polypropylene. Each of the compartments 33 is structured to accommodate a contact lens immersed in a lens care solution. The contact lenses are manufactured using materials and techniques known in the art and not discussed further herein. The lid 37 lies flat on the base portion 35 of the pod 31, covering the compartments 33. The lid 37 may be partially but not wholly peeled from the base portion 35 by the user. The lid 37 is attached to the base 35 by a permanent seal 70 along one longer edge of the pod 31. The remainder of the lid 37 is re-sealable and may be in a sealed, unsealed, or re-sealed condition. The lid 37 does not crease when it is peeled back (similar to a yoghurt pot lid), so that the lid 37 returns to its original (unpeeled) position when it is replaced. In manufacturing, the initial seal of the lid 37 to the base portion 35 is formed by compression, with more compression used to form the permanent seal 70 than the temporary (re-sealable) seal. The case 1 utilises the same mechanism (compression) to re-seal the lid 37 to the base portion 35. In some situations, heat may be used to adhere the polypropylene of the film lid to the base member during the compression stage.

Figure 9:
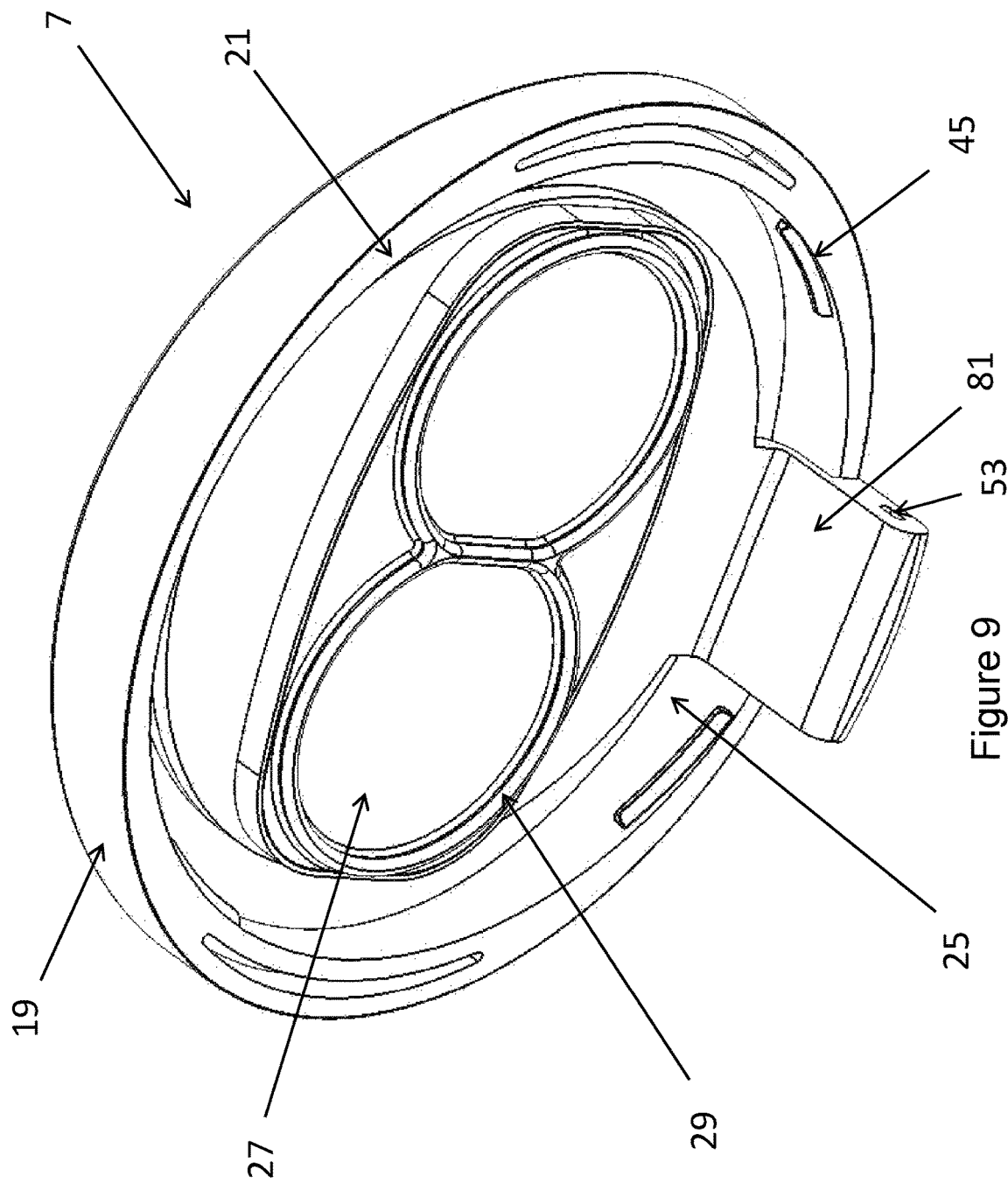
FIG. 9 is a perspective view of the upper part of the example case of FIG. 1 showing the rubber insert in the upper part.
Figure 10:
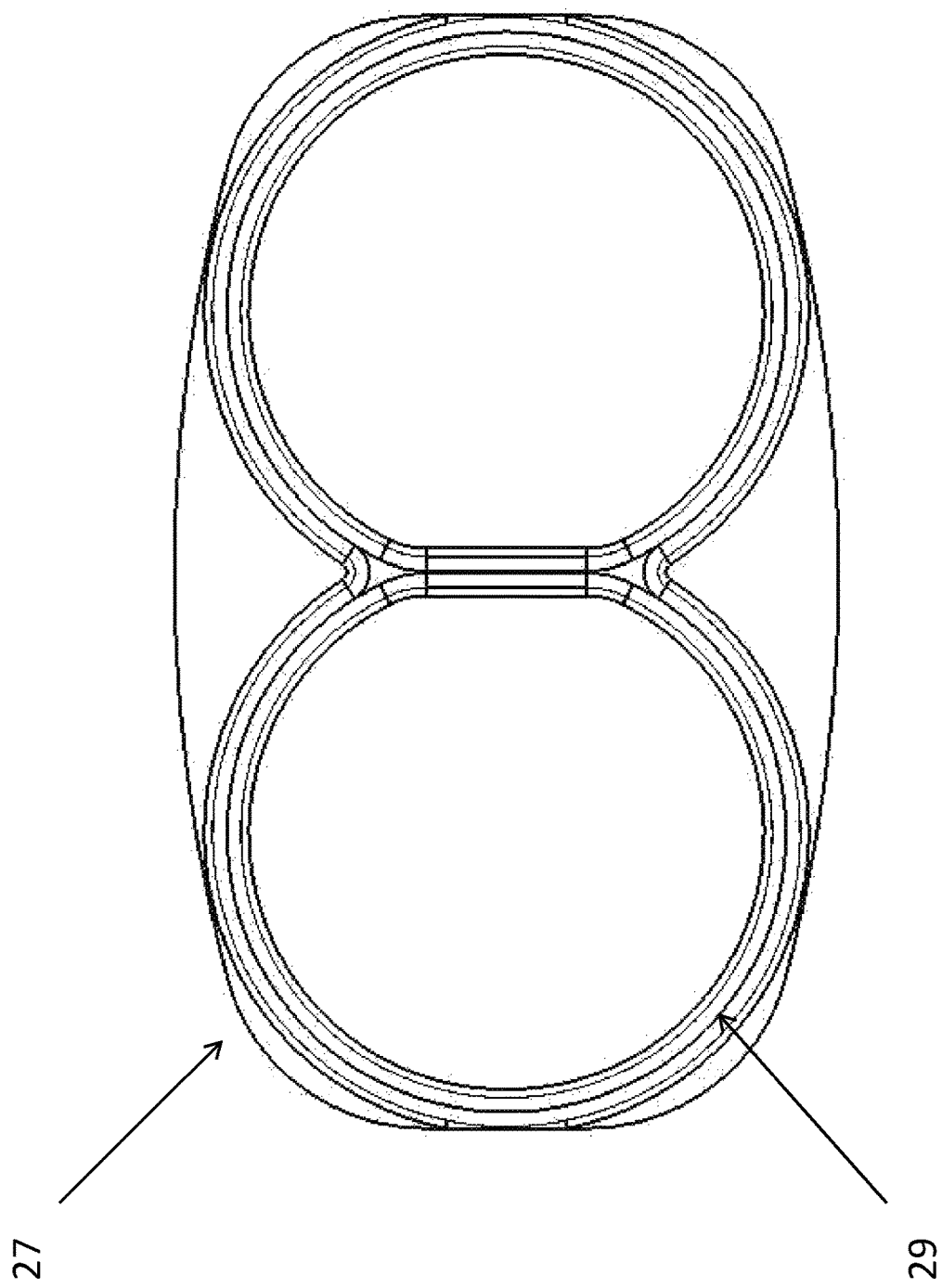
FIG. 10 is a bottom view of the rubber insert of FIG. 9.

In the third arrangement, the user can also see some of the inner components of the upper part 7 (see FIG. 9). The upper part 7 has a cover 19 over a compression member 21. The compression member 21 includes a plunger 25 supporting a rubber insert 27. The rubber insert 27 is sized and shaped to fit over the film lid 37 of the pod 31 when the case 1 is closed (i.e. moved to the second then to the first arrangement). The lower surface of the rubber insert 27 (see FIG. 10) has ridges 29 in a generally figure-eight configuration, extending across the length of the insert 27 and sized and shaped to fit around the compartments 33 of the pod 31. The inner pod may be coloured to distinguish it from a differently coloured pod containing a different solution. The upper surface (not shown) of the rubber insert 27 is planar.

Figure 11:
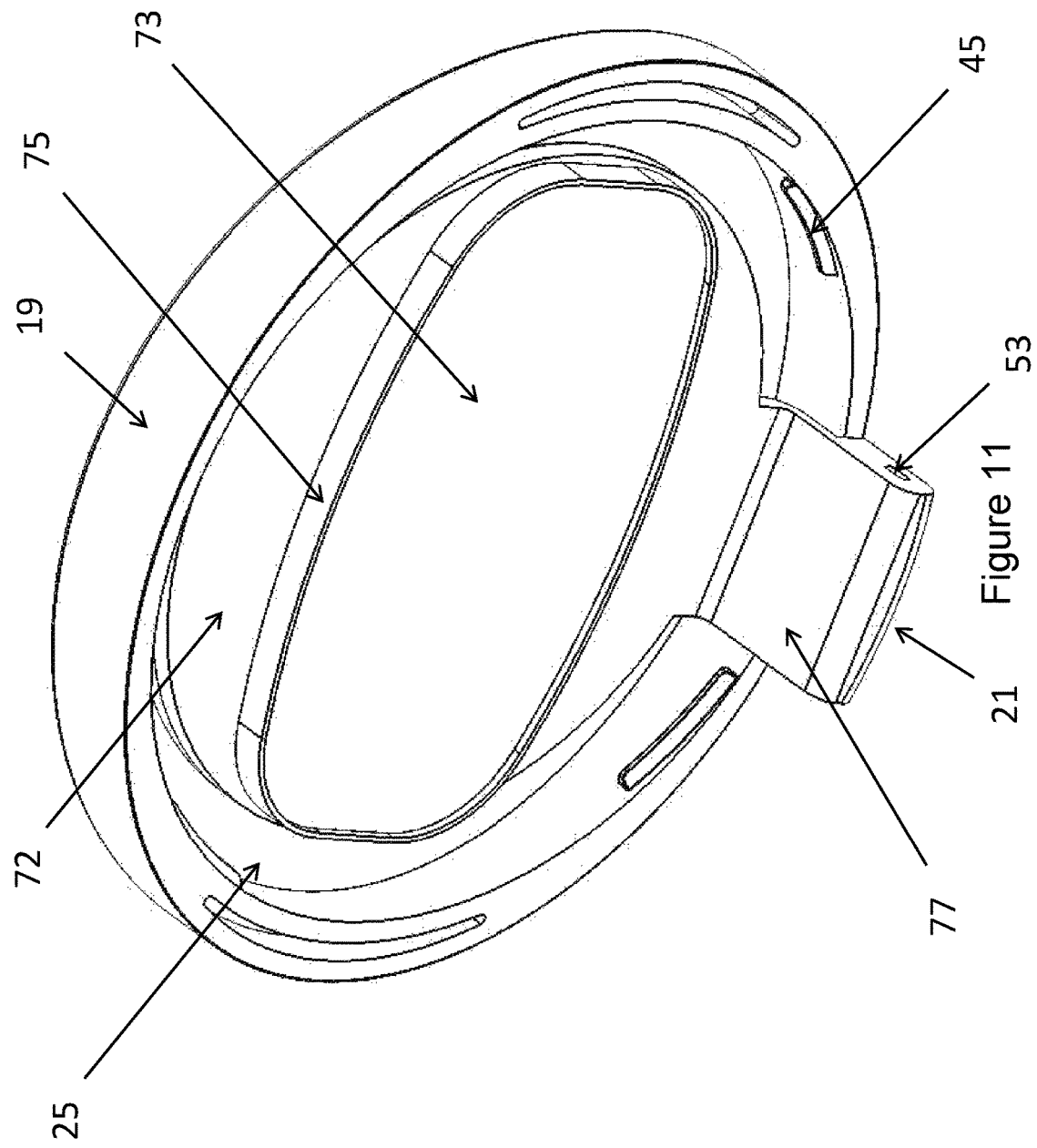
FIG. 11 is a perspective view of a cutaway of the upper part of the example case of FIG. 1, showing part of the internal structure and in particular the plunger in the upper part.
Figure 12:
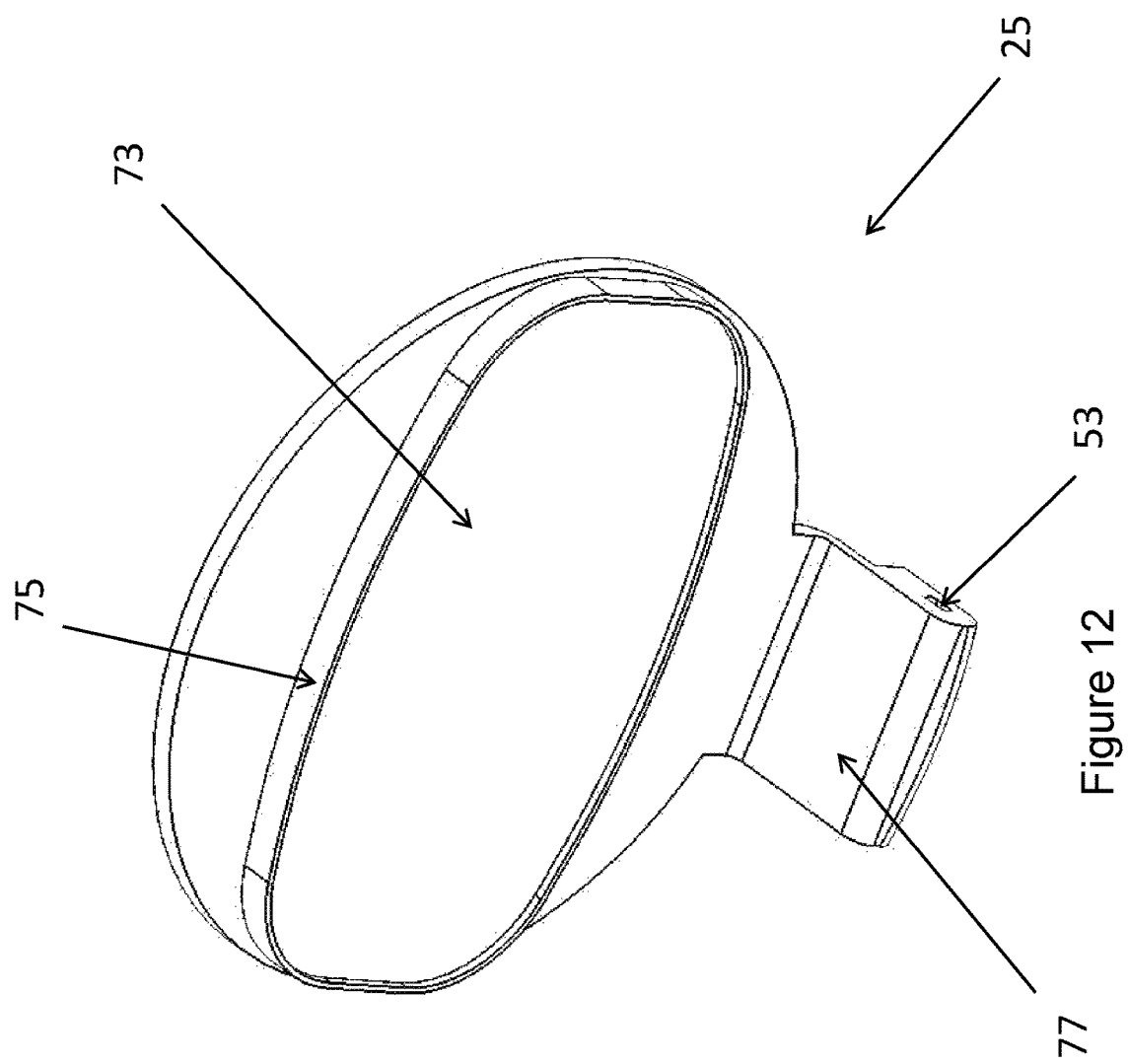
FIG. 12 is a perspective view of the plunger of FIG. 11.

FIG. 11 shows the upper part 7 with the rubber insert 27 removed so that the plunger 25 is more clearly visible (see also FIG. 12). The plunger 25 is an L-shaped plastic member with a circular platform 72 and an arm 77. The circular platform 72 has a central planar portion 73 bounded by a wall 75. The rubber insert 27 is sized and shaped to fit snugly within the wall 75 and rest flush against the central planar portion 73, so that uniform contact is made between the plunger 25 and rubber insert 27. That central planar portion 73 pushes on the rubber insert 27, which pushes on the film lid 37 of the pod 31 when the case 1 is moved from the second to the first arrangement. The wall 75 holds the rubber insert 27 in place.

The arm 77 is sized to fit within the recessed portion 79 (see FIG. 6) of the lower part 9 to form the hinge. The axle of the hinge (not shown) passes through a void 53 in the arm 81 of the plunger 25. The threaded portions 45 form a partial helix around the outside of the rubber insert 27, and are positioned to fit with the corresponding threaded portions 47 of the lower part 9.

Figure 13:
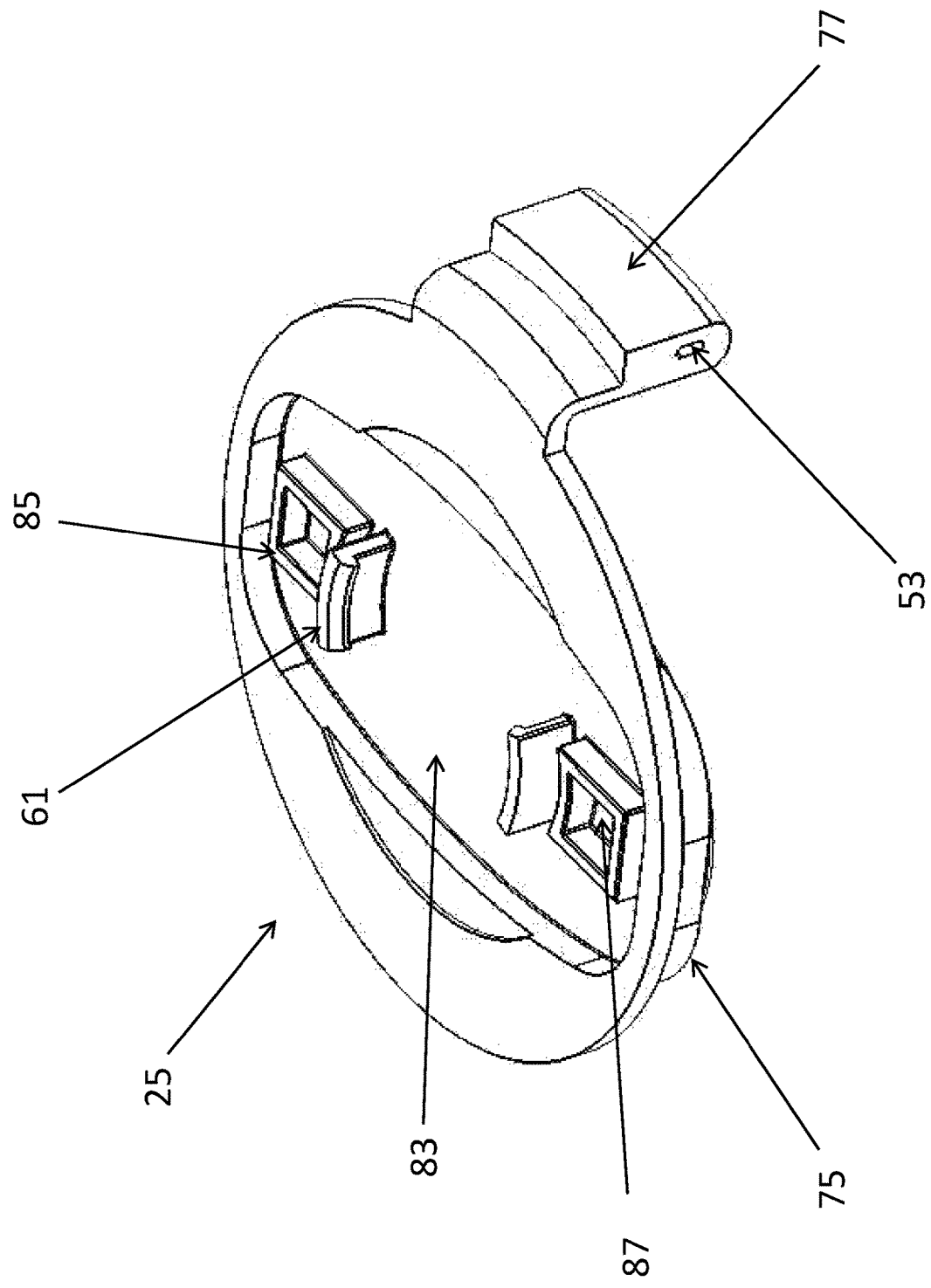
FIG. 13 is an alternative perspective view of the plunger of FIG. 11, showing the hinge channel.

The upper side of the plunger 25 (see FIG. 13) has a central recessed region 83 in which two built-up walls 85 are positioned (built up to the top of the recess), each defining a square compartment 87. Positioned inwards of the built-up walls 85 are two retaining clips 61 for holding the cover 19 to the plunger 25.

Figure 14:
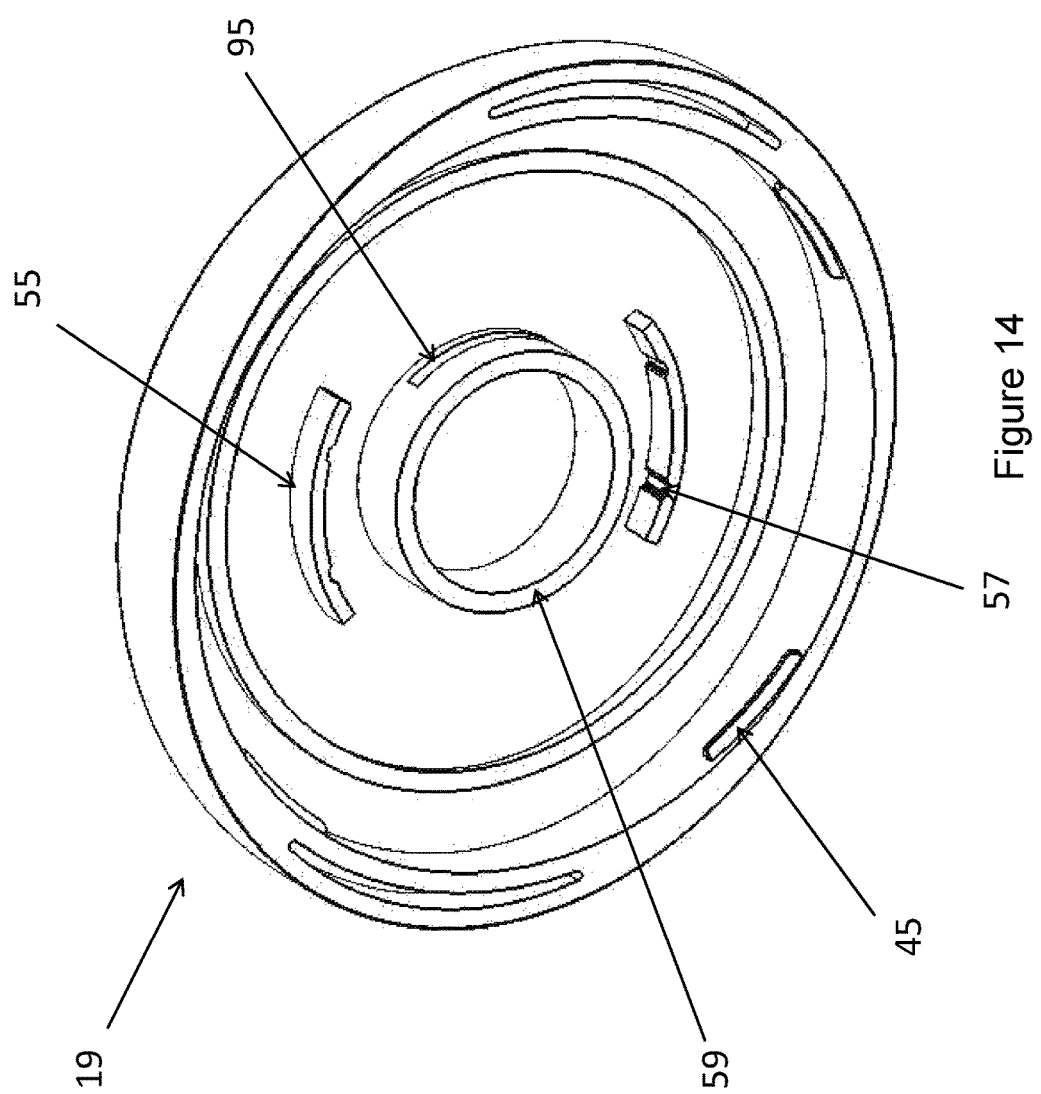
FIG. 14 is a perspective view of the cover of the example case of FIG. 1.

FIG. 14 shows the cover 19 of the upper part 7 with the plunger 25, annulus 23 and rubber insert 27 removed so that only the cover 19 is visible. On the underside of the cover 19 are two raised arcuate walls 55. Each arcuate wall 55 has two recesses 57, one at each end, on the inner surface of each wall 55. Inside of the raised arcuate walls 55 is a raised rigid ring 59, with height greater than the raised arcuate walls 55. The raised rigid ring 59 is sized and shaped to connect with the recessed surface 83 on the upper side of the plunger 25. The ring 59 has two rectangular holes 95 at its base, sized and shaped to accommodate the retaining clips 61 fixed to the upper side of the plunger 25.

Figure 15:
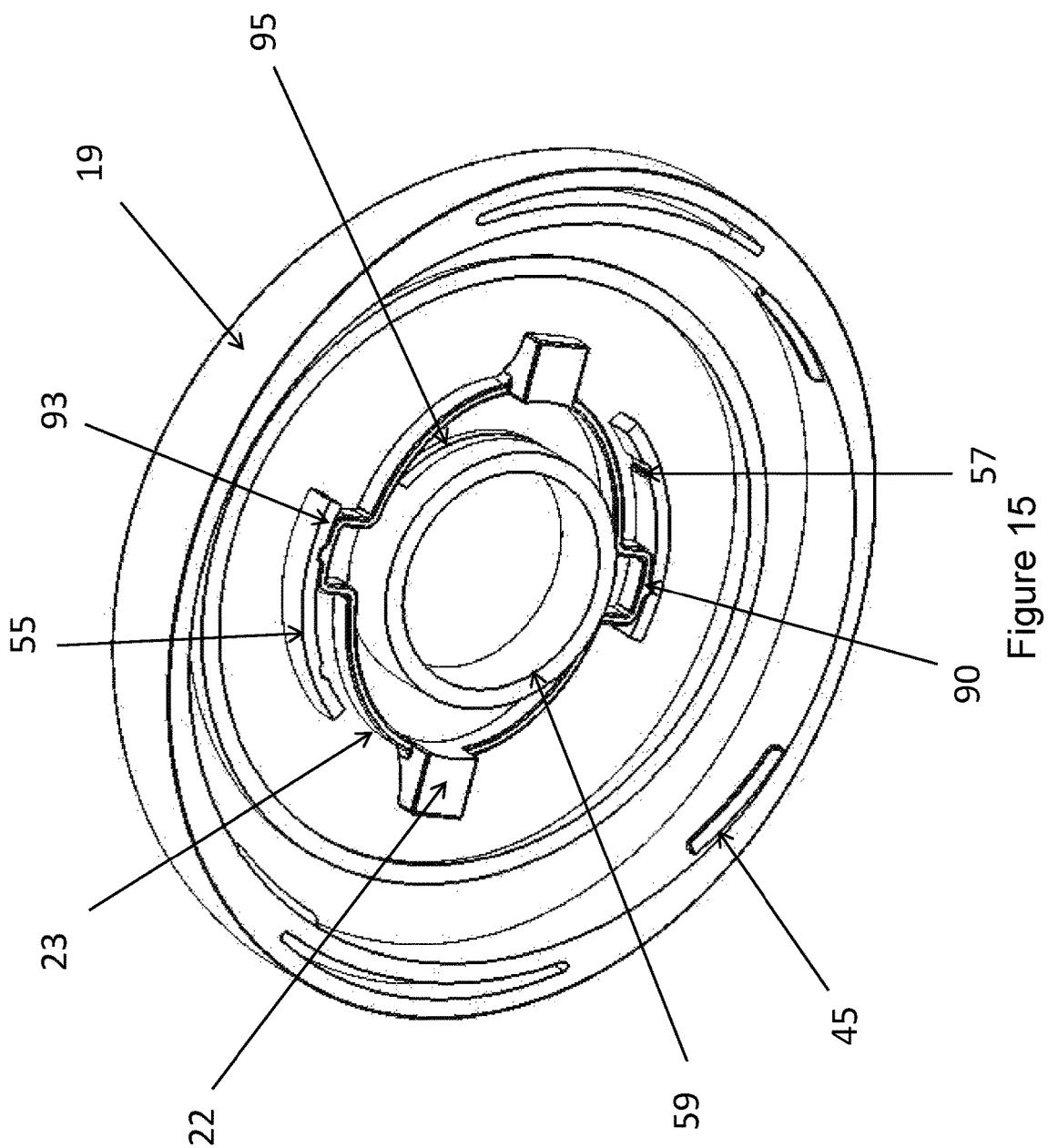
FIG. 15 is a perspective view of a cutaway of the upper part of the example case of FIG. 1, showing part of the internal structure and in particular the annulus in the cover of FIG. 14.

FIG. 15 shows the cover 19 of the upper part 7 of FIG. 14 but with the annulus 23 installed. The annulus 23 is a raised rigid ring and is positioned centrally on the underside of the cover 19 (but is movable with respect to the cover 19). The annulus 23 is positioned radially inside of the raised arcuate walls 55 and outside of the raised rigid ring 59. The annulus 23 has four protrusions spaced equally around the annulus 23. On opposite sides of the annulus 23 are two protruding solid square blocks 22 which extend radially out and vertically down from the annulus 23 and which fit snugly within the square compartments 87 on the upper side of the plunger 25 (see FIG. 13), holding the annulus 23 fixedly to the plunger 25. Equidistant between the square blocks 22, are two hollow square protrusions 93 resembling deformations in the circular form of the annulus 23. On the outer surface of each hollow square protrusion (deformation) 93, i.e. facing the inner surface of the raised arcuate walls 55, is a single protrusion 90. The protrusion 90 on each deformation 93 is sized and shaped to fit in the recesses 57 of the raised arcuate walls 55.

The Mechanisms

Figure 16:
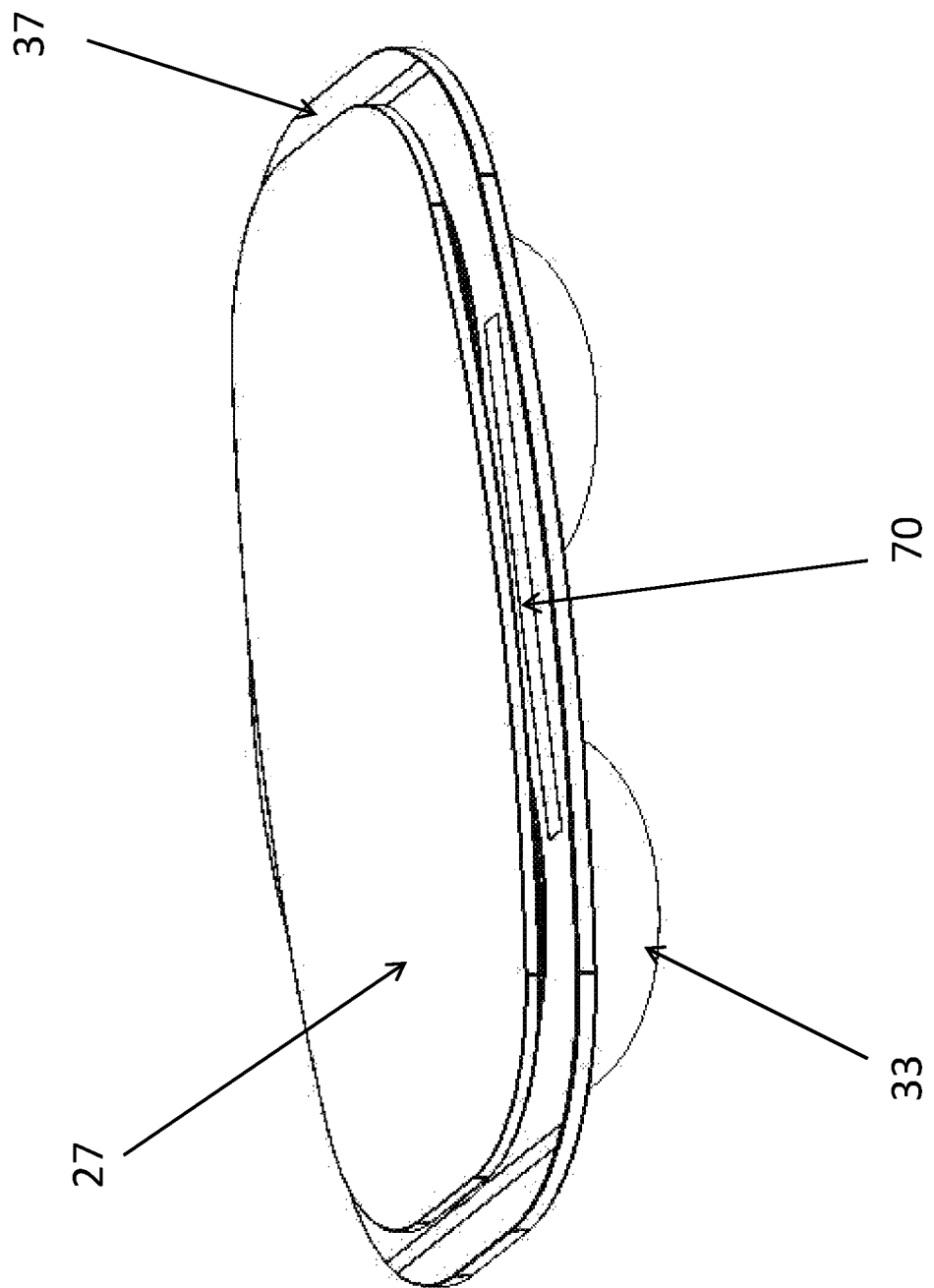
FIG. 16 is a perspective view of the inner pod in contact with the rubber insert of the example case of FIG. 1.

The ridges 29 of the rubber insert 27 (FIG. 10) encircle the compartments of the pod 31. In the disengaged position, the ridges 29 rest above the film lid 37, but in the engaged position they press onto the film lid 37 (see FIG. 16), forming a water-tight seal between the lid 37 and the base portion 35 around the compartments 33.

The components of the case 1 connect via three mechanisms, to seal/un-seal the pod 31.

First, the case 1 is pivotally openable. The upper part 7 and the lower part 9 are separable about the hinge 49 at the perimeter towards the rear of the case 1 (see FIG. 3). The entire upper part 7 rotates about the hinge 49, with the compression member 21 and lower part 9 forming the arms of the hinge 49. In the closed configuration (upper 7 and lower 9 parts closed about the hinge 49), when the user rotates the cover 19 of the case 1 to move it to the engaged position (compressed position), the hinge 49 must accommodate the relative vertical movement of the upper 7 and lower 9 parts. As described above, the hinge 49 has a hinge channel which runs through the compression member 21 and lower part 9, to accommodate the axle (not shown). The channel is formed of an outer portion 51 in the lower part 9 (FIG. 6) and an inner portion 53 in the compression member 21 (FIG. 12). The outer portion 51 is circular, for holding the axle (not shown) in place (FIG. 11). The inner portion 53 has an elongated circular cross-section (being taller than it is wide) allowing the upper part 7 to move vertically up/down with respect to the lower part 9, as the user rotates the cover 19.

Second, the case 1 allows compression of the upper part 7 with respect to the lower part 9. The function is provided by the interlocking threaded portions 45, 47 on the inner surface of the cover 19 and the lower part 9 (see FIGS. 4 and 9, for example). When the cover 19 is rotated clockwise relative to the lower part 9, the threaded portions 45 of the cover 19 move down and into the threaded portions 47 of the lower part 9, holding the case 1 together tightly (the engaged position). This might be said to be similar to the action of screwing a lid onto a jar.

Third, the case 1 allows the cover 19 to rotate with respect to the lower part 9 and compression member 21. The compression member 21 does not rotate with respect to the lower part 9 because it is held by the hinge 49. The annulus 23 acts to decouple the rotational and vertical components of the motion of the cover 19. The annulus 23 is fixed with respect to the compression member 21, being securely held on its upper surface by square grips 22 (FIG. 15). The cover 19 rotates with respect to the annulus 23. The annulus 23 fits onto the guide 55 on the inner surface of the cover 19. The guide has recesses 57 at each end of the rotational arc made by the cover 19 as it screws onto the lower part 9, in which protrusions 90 on the annulus 23 rest. Some force is required by the user therefore to move the cover 19 from the engaged to the disengaged position or vice versa, releasing the annulus 23 from its resting position and moving it towards the other hollow 57. When the cover 19 is screwed onto the lower part 9 the annulus 23 moves across the guide 55. However, the vertical force applied through the screwing action is not transmitted through the annulus 23. Rather, there is a rigid inner rim 59 protruding from the inner surface of the cover 19, located radially inside the annulus 23 and tall enough to contact the compression member 21 in the disengaged position. When the cover 19 is screwed onto the lower part 9, the rigid inner rim 59 applies pressure to the compression member 21. Therefore, during use, the rotational force applied by the user to the upper part 7 to lock the case 1 causes the rubber insert 27 to press down on the lid 37 of the inner pod 31. The rigid inner rim 59 is retained by clips 61 (FIG. 13) which fixes the cover 19 to the compression member 21.

When the cover 19 is screwed onto the lower part 9 (the engaged position), the interlocking threaded portions 45, 47 restrict movement about the hinge 49 so that the case 1 may not be opened. However, when the cover 19 is disengaged so that the threaded portions 45, 47 are not interlocked, the upper part 7 may be freely raised and lowered.

When the cover 19 is screwed onto the lower part 9, the raised rigid ring 59 applies force to the plunger 25. At the same time, the cover 19 rotates with respect to the plunger 25, and as it does so, the arcuate walls 55 move with respect to the annulus 23 so that in effect, the protrusions 90 move between the recesses 57. The raised arcuate walls 55 provide a guide, and limit the extent of the rotation, with the recesses 57 providing resting positions. The space between the recesses 57 represents the maximum extent of rotational displacement. The protrusions 90 are biased to remain in the recesses 57, and only when rotational force is applied (i.e. when the cover is screwed/unscrewed), are the protrusions 90 forced out of the recesses 57 and guided across the arc 55.

Whilst the present invention has been described and illustrated with reference to particular embodiments, it will be appreciated by those of ordinary skill in the art that the invention lends itself to many different variations not specifically illustrated herein. By way of example only, certain possible variations will now be described.

A variation is a case having only one recessed compartment. Alternatively the case may have two or more recessed compartments. Another variation is an alternative location of compression seal, for example formed around the perimeter of the base portion of the inner pod. Another variation is an alternative elastomeric insert design, having no raised ridges or ridges arranged in an alternative pattern.

The present disclosure is described herein with respect to contact lens cases. It will be appreciated that, with appropriate modification, the present apparatus and methods may be useful for cases for other types of ophthalmic lenses.

Where in the foregoing description, integers or elements are mentioned which have known, obvious or foreseeable equivalents, such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

The invention claimed is:

1. A method of treating a contact lens including the following steps:
    providing a case for holding one or more contact lenses, the case comprising an upper part and a lower part wherein the upper part comprises a cover mounted on a compression member, the cover mounted for movement such that the cover rotates with respect to the compression member;
    providing an inner pod comprising a base portion defining one or more compartments and a re-sealable lid;
    partially removing the lid of the inner pod;
    placing a contact lens in a compartment of the inner pod;
    replacing the lid of the inner pod;
    placing the inner pod on the lower part of the case;
    closing the case so that the inner pod is enclosed in the case;
    moving the upper part relative to the lower part by rotating the cover with respect to the compression member so that the inner pod is compressed between the upper and lower parts and the lid seals the one or more compartments to form a water-tight seal between the lid and the base portion.

2. A method of treating a contact lens according to claim 1 including the step of:
    removing a used inner pod from the case and discarding the used inner pod.

3. A method of treating a contact lens including the steps of:
    providing a case for holding one or more contact lenses, the case comprising an upper part and a lower part, wherein the case is in an open arrangement in which the upper and lower parts are pivotally separated;
    providing an inner pod comprising a base portion defining one or more compartments and a re-sealable lid;
    partially removing the lid of the inner pod;
    placing a contact lens in a compartment of the inner pod;
    replacing the lid of the inner pod;
    placing the inner pod on the lower part of the case;
    moving the case from the open arrangement to a closed and disengaged arrangement in which the upper and lower parts are not pivotally separated and the upper and lower parts are misaligned and the inner pod is not compressed between the upper and lower parts;
    moving the case from the closed and disengaged arrangement to a closed and engaged arrangement in which the upper and lower parts are not pivotally separated and the upper and lower parts are aligned and the inner pod is compressed between the upper and lower parts and the lid seals the one or more compartments.

* * * * *